(12) United States Patent
Hammang et al.

(10) Patent No.: US 6,436,427 B1
(45) Date of Patent: *Aug. 20, 2002

(54) DEVICE AND METHOD FOR TREATING OPHTHALMIC DISEASES

(75) Inventors: Joseph P. Hammang, Barrington, RI (US); E. Edward Baetge, St. Sulpice (CH); William G. Tsiarias, Barrington, RI (US); Peter D. Spear, Boulder, CO (US)

(73) Assignee: Neurotech S.A., Evry (FR)

(*) Notice: Subject to any disclaimer, the term of this patent is extended or adjusted under 35 U.S.C. 154(b) by 0 days.

This patent is subject to a terminal disclaimer.

(21) Appl. No.: 09/973,325

(22) Filed: Oct. 9, 2001

Related U.S. Application Data

(63) Continuation of application No. 09/155,066, filed as application No. PCT/US97/04701 on Mar. 24, 1997, now Pat. No. 6,299,895, which is a continuation of application No. 08/620,982, filed on Mar. 22, 1996, now Pat. No. 5,904,144.

(51) Int. Cl.[7] .................................................. A67F 2/00
(52) U.S. Cl. .................................... 424/427; 623/4
(58) Field of Search ............................. 424/427; 623/4

(56) References Cited

U.S. PATENT DOCUMENTS

| | | |
|---|---|---|
| 3,828,777 A | 8/1974 | Ness |
| 4,164,559 A | 8/1979 | Miyata et al. |
| 4,186,184 A | 1/1980 | Zaffaroni |
| 4,300,557 A | 11/1981 | Refojo et al. |
| 4,343,787 A | 8/1982 | Katz |
| 4,730,013 A | 3/1988 | Bondi et al. |
| 4,740,461 A | 4/1988 | Kaufman |
| 4,853,224 A | 8/1989 | Wong |
| 4,863,457 A | 9/1989 | Lee |
| 4,968,733 A | 11/1990 | Muller et al. |
| 4,976,859 A | 12/1990 | Wechs |
| 4,997,929 A | 3/1991 | Collins et al. |
| 5,098,443 A | 3/1992 | Parel et al. |
| 5,122,464 A | 6/1992 | Wilson et al. |
| 5,141,856 A | 8/1992 | Collins et al. |

(List continued on next page.)

FOREIGN PATENT DOCUMENTS

| | | |
|---|---|---|
| EP | 338 841 | 10/1989 |
| WO | WO 92/19195 | 11/1992 |
| WO | WO 93/06116 | 4/1993 |
| WO | WO 94/24870 | 11/1994 |
| WO | WO 95/05452 | 2/1995 |
| WO | WO 95/13765 | 5/1995 |
| WO | WO 95/13765 | 10/1995 |
| WO | WO 95/29242 | 11/1995 |
| WO | WO 95/30686 | 11/1995 |
| WO | WO 95/02646 | 2/1996 |

OTHER PUBLICATIONS

Adamis, et al. (1994). *Am. J. Ophthamol.* 118: 445–450.
Adamis, et al. (1996). *Arch. Opthalmol.* 114: 66–71.
"Advances in Glaucoma Therapy." *Drug and Market Development* 5(9–10): 272–287.

(List continued on next page.)

*Primary Examiner*—Carlos Azpuru
(74) *Attorney, Agent, or Firm*—Mintz, Levin, Cohn, Ferris, Glovsky and Popeo, P.C.; Ivor R. Elrifi, Esq.; Christina V. Karnakis, Esq.

(57) ABSTRACT

The invention provides a method for delivering biologically active molecules to the eye by implanting biocompatible capsules containing a cellular source of the biologically active molecule. Also provided is a method of treating ophthalmic diseases using biocompatible capsules.

7 Claims, 4 Drawing Sheets

U.S. PATENT DOCUMENTS

| | | | |
|---|---|---|---|
| 5,147,647 A | | 9/1992 | Darougar |
| 5,158,881 A | | 10/1992 | Aebischer et al. |
| 5,164,188 A | | 11/1992 | Wong |
| 5,185,152 A | | 2/1993 | Peyman |
| 5,266,562 A | | 11/1993 | Mukherjee et al. |
| 5,279,298 A | | 1/1994 | Flower |
| 5,284,761 A | | 2/1994 | Aebischer et al. |
| 5,300,114 A | | 4/1994 | Gwon et al. |
| 5,322,691 A | | 6/1994 | Darougar et al. |
| 5,364,769 A | | 11/1994 | Rosenthal |
| 5,378,475 A | | 1/1995 | Smith et al. |
| 5,382,514 A | | 1/1995 | Passaniti et al. |
| 5,384,333 A | | 1/1995 | Davis et al. |
| 5,395,618 A | | 3/1995 | Darougar et al. |
| 5,443,505 A | | 8/1995 | Wong et al. |
| 5,453,361 A | | 9/1995 | Yancopoulos et al. |
| 5,466,233 A | | 11/1995 | Weiner et al. |
| 5,472,436 A | | 12/1995 | Femstad |
| 5,476,511 A | | 12/1995 | Gwon et al. |
| 5,521,215 A | | 5/1996 | Mechoulam et al. |
| 5,550,050 A | * | 8/1996 | Holland et al. .......... 435/240.2 |
| 5,904,144 A | * | 5/1999 | Hammang et al. .......... 128/898 |
| 6,299,895 B1 | * | 10/2001 | Hammang et al. .......... 424/427 |

OTHER PUBLICATIONS

Aebischer, et al. (1994). *Transplantation* 58 (11): 1275–1277.
Aiello, et al. (1995). *Proc. Natl. Acad. Sci. USA* 92: 10457–10461.
Anand, et al. (1993). *Arch. Ophthalmol.* 111: 223–227.
Ashton. "Retinal Vascularization in Health and Disease". *Protor Award Lecture of the Association for Research in Opthalmology.*
Baetge, et al. (1988). *Proc. Natl. Acad. Sci. USA* 85(10): 3648–3652.
Baetge, et al. (1986). *Proc. Natl. Acad. Sci. USA* 83(15): 5454–5458.
Besnard, et al. (1991). *J. Biological Chem.* 266(28): 18877–18883.
Brooks, et al. (1994). *Science* 264: 569–571.
Colton and Lowrie (1981). *The Kidney.* pp. 2425–2489.
De Araujo and Linden (1993). *Euro. J. Neurosci.* 5: 581–597.
De Juan, et al. (1990). *Invest. Ophthalmol. Vis. Sci.* 31(7): 1238–1244.
De Vos, et al. (1992). *Current Eye Res.* 11(6):581–597.
Dirks, et al. (1993). *Gene* 128(2): 247–249.
Ezekowitz, et al. (1992). *New England J. Med.* 326(22): 1456–1463.
Faktorovich, et al. (1990). *Nature* 347:83–86.
Folkman (1995). *Seminars in Medicine Beth Israel Hosp.* 333(26): 1757–1763.
Friedlander, et al. (1995). *Science* 270: 1500–1502.
Fung (1991). *Am. J. Ophthalmol.* 112(3): 349–350.
Gillies, et al. (1993). *Br. J. Ophthalmol.* 77: 759–765.
Golden, et al. (1995). *Proc. Natl. Sci. USA* 92: 5704–5708.
Grant, et al. (1986). *Diabetes* 35: 416–420.
Grant, et al. (1993). *Diabetologia* 36: 282–291.
Grant, et al. (1986). *J. Clinical Endocrinol Metabolism* 63(4): 981–984.
Guyer, et al. (1992). *Arch. Ophthalmol.* 110: 1383–1384.
Hammang, et al. (1994). *Methods Neurosci.* 21:281–293.
"Ingenuity Abounds as Researchers Explore New Ways of Delivering Medication to Eye." (1988). *JAMA* 260(24): 3556.
Johansson, et al. (1995). *Exp. Neurol.* 134:25–34.
Kaneda, et al. (1991). *Neuron.* 6(4): 583–594.
Kaplan and Streilein (1978). *J. Immonol.* 120(3): 689–693.
Keck, et al. (1989). *Science* 246: 1309–1312.
Kirkpatrick, et al. (1993). *Br. J. Ophthalmol.* 77: 766–770.
Koide, et al. (1995). *Neurosci. Lett.* 185: 183–186.
Lacy, et al. (1991). *Science* 254: 1782–1784.
LaVail, et al. (1992). *Proc. Natl. Acad. USA* 89: 11249–11253.
Leff (1995). *BioWorld Today* 6(214): 1,3.
Lemke, et al. (1988). *Neuron* 1: 77–83.
Leung, et al. (1989). *Science* 246: 1306–1309.
Lincoff, et al. (1993). *Investig. Ophthalmol. Vis. Sci.* (Abstract Issue) 34(4): 1160.
Lincoff, et al. (1993) *Investig. Ophthalmol. Vis. Sci.* (Abstract Issue) 33(4): 729.
Lincoff, et al. (1991). *Invsetig. Ophthalmol. Vis. Sci.* (Abstract Issue) 32(4): 674.
Liu, et al. (1987). *Investig. Ophthalmol. Vis. Sci.* *17(10): 933–1004.
Liu, et al. (1987). *Ophthalmol.* 94(9): 1155–1159.
Liu, et al. (1983). *Br. J. Ophthalmol.* 67:479–484.
Macejak and Sarnow (1993). *Nture* 353: 90–94.
Malecaze, et al. (1994). *Arch. Ophthalmol.* 112: 1476–1482.
Martin, et al. (1994). *Arch. Ophthalmol.* 112: 1531–1539.
Martinez–Salas, et al. (1993). *J. Virology* 67(7): 3748–3755.
Mercer, et al. (1991). *Neuron* 7: 703–716.
Miller, et al. (1994). *Am. J. Pathol.* 145(3): 574–584.
Misbin, et al. (1987). *J. Clin. Endocrinol. Metabolism* 64(5): 964–968.
Mooney (1988). *Irish J. Medical Sci.* 157(7): 34–39.
Morley, et al. (1995). *Ophthalmol.* 102:(3): 388–392.
Mountford, et al. (1994). *Proc. Natl. Acad. Sci. USA* 91: 4303–4307.
Nakahira, et al. (1990). *J. Biological Chem.* 265(32): 19786–19791.
Nicolini, et al. (1990). *Circulation* 81(3): 1115–1122.
Osulsky, et al. (1995). *Graefe's Arch. Clin. Exp. Ophthalmol.* 223: 220–225.
Perez and Caminos (1995). *Neurosci. Lett.* 183: 96–99.
Poliner, et al. (1993). *Ophthalmol.* 100(9): 1417–1424.
Rabacchi, et al. (1994). *Neurosci.* 63(4): 969–973.
Ray, et al. (1993). *Proc. Natl. Acad. Sci. USA* 90(8): 3602–3606.
"Regeneron's Neurotrophic Factors Prevent Degeneration of Eye Retina Cells" (1993). *Genet. Technol. News.* 13: 2.
Reynolds and Weiss (1992). *Science* 255: 1707–1710.
Richards, et al. (1992). *Proc. Natl. Acad. Sci. USA* 89(18): 8591–8595.
Sadun (1990). *Metabolic, Pediatric and Systematic Ophthalmol.* 13: 79–84.
Sakimura, et al. (1987). *Gene* 60: 103–113.
Sanborn, et al. (1992). *Arch. Ophthalmol.* 110: 188–195.
Shell (1974). *Ophthalmic Surgery* 5(3): 73–77.
Shweiki, et al. (1992). *Nature* 359: 843–848.
Sidky and Borden (1987). *Cancer Res.* 47: 5155–5161.
Siliprandi, et al. (1993). *Ivestig. Ophthalmol. Vis. Sci.* 34(12): 3232–3245.
Smiddy, et al. (1990). *Retina* 10:(4): 288–296.
Smith, et al. (1992). *Arch. Ophthalmol.* 110: 255–258.
Southern (1982). *In Vitro* 18(3): 515.
Southern and Berg (1982). *J. Mol. App. Genet.* 1(4): 327–341.
Steinert, et al. (1991). *Am. J. Ophthalmol.* 112: 373–380.

Stone, et al. (1995). *Neurosci.* 15(7): 4738–4747.
Stout (1995). *Ophthalmol.* 102(10): 1415–1416.
Thomas and Ibanez (1993). *Am. J. Ophthalmol.* 115: 563–568.
Tripathi and Tripathi (1983). *Biomedical Found Ophthalmol.* 1: 1–88.
White, et al. (1989). *New England J. Med.* 320(18): 1197–1200.
Winn, et al. (1994). *Proc. Natl. Acad. Sci. USA* 91(6): 2324–2328.
PCT, International Search Report for PCT/US 97/04701. Issued on Aug. 9, 1997.
Paul (1999). *Fundamental Immunology* 21: 741–773.
Paul (1999). *Fundamental Immunology* 22: 775–811.

* cited by examiner

DEVICE AND METHOD FOR TREATING OPHTHALMIC DISEASES

This application is a continuation of U.S. patent application Ser. No. 09/155,066 filed on Sep. 21, 1988 now U.S. Pat. No. 6,297,895, which is a 371 of PCT/US97/04701, filed Mar. 24, 1997 which is a continuation of U.S. patent application Ser. No. 08/620,982 filed Mar. 22, 1996, Now U.S. Pat. No. 5,904,144, issued May 18, 1999, each of which is incorporated by reference in its entirety.

TECHNICAL FIELD OF THE INVENTION

This invention relates to devices and methods for treatment of ophthalmic diseases and disorders using encapsulated cells for intraocular and periocular delivery of biologically active molecules.

BACKGROUND OF THE INVENTION

There are a number of vision-threatening disorders of the eye for which there are presently no good therapies. One major problem in treatment of such diseases is the inability to deliver therapeutic agents into the eye and maintain them there at therapeutically effective concentrations.

Oral ingestion of a drug or injection of a drug at a site other than the eye can provide a drug systemically. However, such systemic administration does not provide effective levels of the drug specifically to the eye. In many ophthalmic disorders involving the retina, posterior tract, and optic nerve, adequate levels of drug cannot be achieved or maintained by oral or parenteral routes of administration. Further, repeated administration of the drug may be necessary to achieve these concentrations. However, this may produce undesired systemic toxicity. For example, subcutaneously or intramuscularly administered alpha-interferon in adults may result in complications such as flu-like symptoms with fatigue, anorexia, nausea, vomiting, thrombocytopenia, and leukopenia.

Ophthalmic conditions have also been treated using drugs applied directly to the eye in either liquid or ointment form. This route of administration however is only effective in treating problems involving the superficial surface of the eye and diseases which involve the cornea and anterior segment of the eye. Topical administration of drugs is ineffective in achieving adequate concentrations of drug in the sclera, vitreous, or posterior segment of the eye. In addition, topical eye drops may drain from the eye through the nasolacrimal duct and into the systemic circulation, further diluting the medication and risking unwanted systemic side effects. Furthermore, the drug is administered indiscriminately to all tissue compartments of the eye, including those that may not need the medication and may in fact suffer unwanted side effects to the drug.

Delivery of drugs in the form of topical eye drops is also of little utility when the drug is a protein or peptide that lacks the ability to cross the cornea and be made available to the vitreous, retina, or other subretinal structures such as the retinal pigment epithelium ("RPE") or choroidal vasculature. In addition, many proteins or peptides are highly unstable and are therefore not easily formulated for topical delivery.

Direct delivery of drugs into the eye by topical insert has also been attempted. However, this method is not desirable. Topical inserts require patient self-administration and thus education on insertion and removal. This demands a certain degree of manual dexterity, which can be problematic for geriatric patients. In many instances such inserts may cause eye irritation. These devices are prone to inadvertent loss due to lid laxity. In addition, these devices provide drug only to the cornea and anterior chamber, and do not provide any pharmacologic advantage over eye drops.

Another extraocular insert is a contact lens delivery system that releases medication over an extended period. See, e.g., *JAMA*, 260:24, p. 3556 (1988). The lens generally only lasts for a matter of hours or days before dissolving or releasing all of the therapeutic compound. Continuous delivery of medication is inconvenient, requiring frequent re-application. Again, these contact lenses only provide drug to the cornea and anterior chamber.

In rare cases, direct delivery of drugs has also been accomplished using extemraliz tubes. This requires insertion of one end of a tube into the corner of the patient's eye. The other end of the tube is taped to the patient's forehead and terminates in a septum, through which medication is delivered. This method is undesirable, being both uncomfortable and inconvenient. Since medication must be injected through the septum, the device is incapable of continuous delivery of medication. Furthermore, such tubes may become infected and in some cases ultimately threaten the patient's vision.

Direct delivery of drugs can also be accomplished by the intraocular injection of the drug, or microspheres that contain the drug. However, microspheres tend to migrate within the eye, either into the visual axis or into adjacent tissue sites.

Most previous intraocular inserts for direct delivery of drugs into the eye have been unsuccessful either because they are unsuitable for long-term use or are uncomfortable to use. For example, the ocular device disclosed in U.S. Pat. No. 3,828,777 is not anchored into position, thus causing pain, irritation, foreign body sensation, retinal detachments, and watering when the device moves. Other ocular inserts disclosed in patents do not disclose sizes or shapes that would allow long-term retention of the insert. See, e.g., U.S. Pat. No. 4,343,787; U.S. Pat. No. 4,730,013; U.S. Pat. No. 4,164,559. Even in patents asserting an improved retention and prolonged period of use, the contemplated period is measured in days, such as 7 to 14 days. See, e.g., U.S. Pat. No. 5,395,618.

One intraocular insert is currently available for delivery of ganciclovir to the eye. Known as Vitrasert, the device consists of a nonerodible, polymer-based, sustained-release package containing ganciclovir, a non-proteinaceous nucleoside analog. The device is surgically implanted in the vitreous humor of the eye to treat cytomegalovirus retinitis. See, e.g., Anand, R., et al., *Arch. Ophthalmol.*, 111, pp. 223–227 (1993).

Another intraocular insert is disclosed by U.S. Pat. No. 5,466,233. This tack-shaped device is surgically implanted so that the head of the tack is external to the eye, abutting the scleral surface. The post of the tack crosses the sclera and extends into the vitreous humor, where it provides for vitreal drug release.

However, release of proteins from such devices (or other erodible or nonerodible polymers) can be sustained for only short periods of time due to protein instability. Such devices are unsuitable for long-term delivery of most, if not all, protein molecules.

Clinical treatment for retinal and choroidal neovascularization includes destruction of new vessels using photocoagulation or cryotherapy. However, side effects are numerous and include failure to control neovascularization, destruction of macula and central vision, and decrease in peripheral vision. See, e.g., Aiello, L. P., et al., *PNAS*, 92, pp. 10457–10461 (1995).

A number of growth factors show promise in the treatment of ocular disease. For example, BDNF and CNTF have been shown to slow degeneration of retinal ganglion cells and photoreceptors in various animal models. See, e.g., *Genetic Technology News*, vol. 13, no. 1 (January 1993). Nerve growth factor has been shown to enhance retinal ganglion cell survival after optic nerve section and has also been shown to promote recovery of retinal neurons after ischemia. See, e.g., Siliprandi, et al., *Invest. Ophthalmol. & Vis. Sci.*, 34, pp. 3232–3245 (1993).

Direct injection of neurotrophic factors to the vitreous humor of the eye has been shown to promote the survival of retinal neurons and photoreceptors in a variety of experimentally induced injuries as well as inherited models of retinal diseases. See, e.g., Faktorovich et al., *Nature*, vol. 347 at 83 (Sep. 6, 1990); Siliprandi et al., *Investigative Ophthalmology and Visual Science*, 34, p. 3222 (1993); LaVail et al., *PNAS*, 89, p. 11249 (1992); Faktorovich et al., *Nature*, 347, pp. 83–86 (1990).

However, previous methods of delivery of such neurotransminers, growth factors, and neurotrophic factors have significant drawbacks. Some problems stem from the fact that growth factors do not cross the blood-brain barrier well and are readily degraded in the bloodstream. Further, problems arise with direct injection into the vitreous. For example, direct injection of bFGF resulted in an increased incidence of retinal macrophages and cataracts. See LaVail, *PNAS*, 89, p. 11249 (1992).

Accordingly, delivery of biologically active molecules to the eye without adverse effects remains a major challenge.

SUMMARY OF THE INVENTION

This invention provides a novel method of treating ophthalmic diseases and disorders by intraocular and periocular delivery of a continuously-produced source of a suitable biologically active molecule ("BAM").

A capsule containing a cellular source of the BAM is surgically placed in the desired location in the eye.

The capsule jacket comprises a membrane surrounding the encapsulated cells and interposes a physical barrier between the cells and the patient. The capsule may be retrieved from the patient.

DETAILED DESCRIPTION OF THE INVENTION

Figure 1:
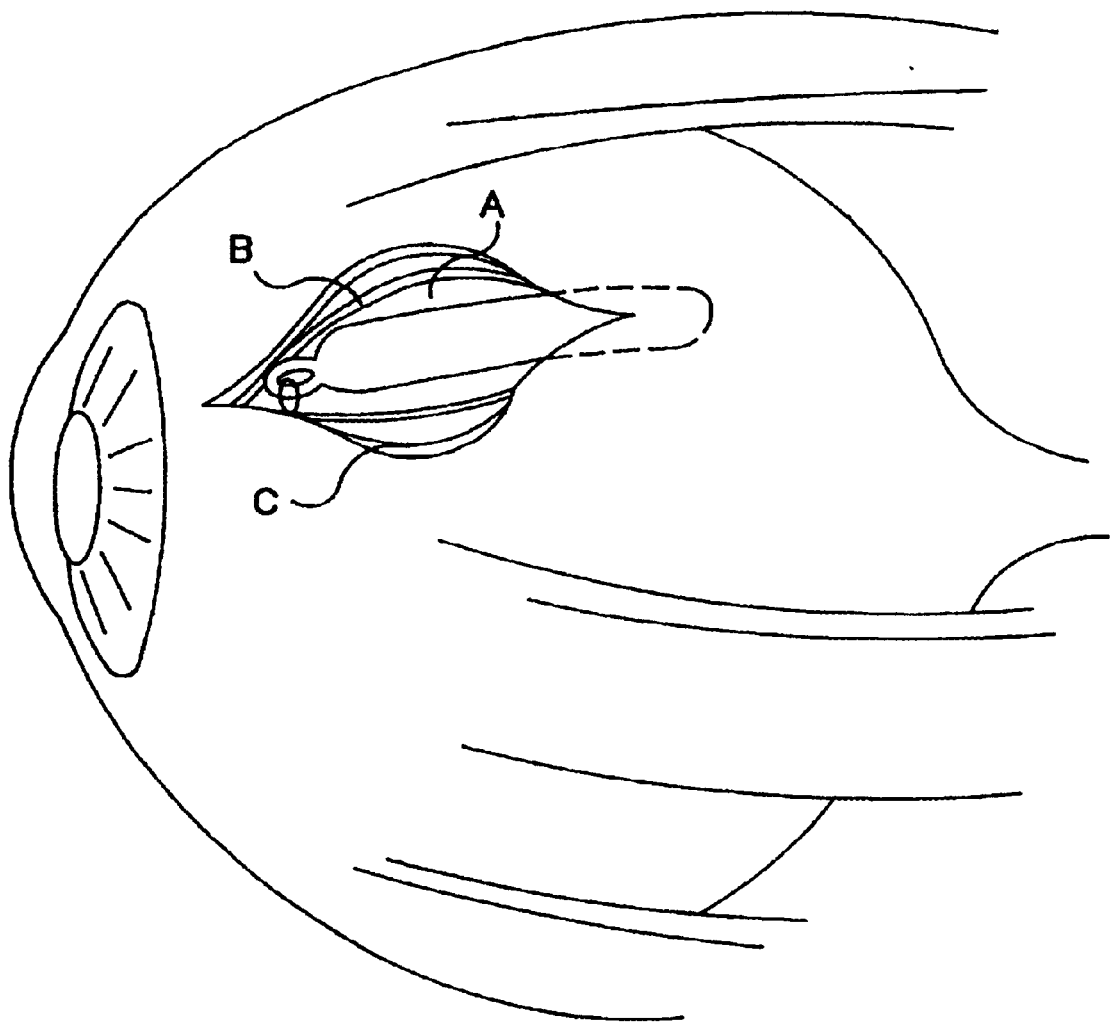
FIG. 1 is a schematic diagram of a horizontal cross section of the eye, indicating a macrocapsule implanted in the vitreous. The diagram is not to scale, and for the sake of clarity shows the capsule in an approximate placement—when actually placed in the human eye, the preferred vitreous placement is in the anterior portion of the vitreous. The letter "A" refers to the sciera, "B" refers to Tenon's capsule, and "C" refers to the conjunctiva.
Figure 2:
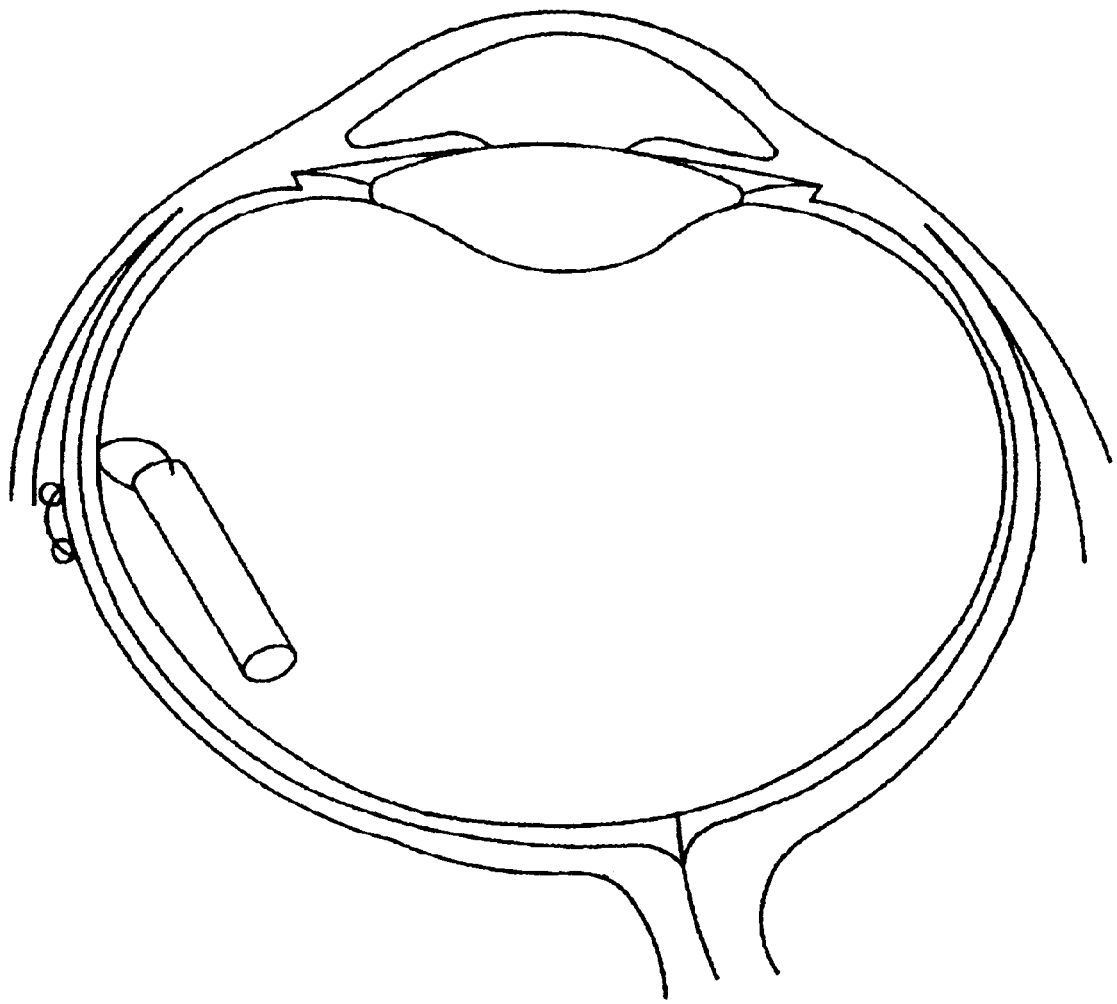
FIG. 2 is a schematic diagram of a side view of the eye showing an implanted capsule beneath Tenon's capsule.

This invention relates to delivery of biologically active molecules ("BAMs") intraocularly (e.g., in the anterior chamber, posterior chamber, or vitreous) or periocularly (e.g., within or beneath Tenon's capsule), or both. The invention may be useful in providing controlled and sustained release of BAMs effective in treating various ophthalmic disorders, ophthalmic diseases, or diseases which have ocular effects.

The devices and techniques of this invention provide numerous advantages over other delivery routes:

Drug can be delivered to the eye directly, reducing or minimizing unwanted peripheral side effects; very small doses of drug (nanogram or low nicrogram quantities rather than milligrams) can be delivered compared with topical applications, also potentially lessening side effects; the viable cells of the devices continuously produce newly synthesized product, avoiding the fluctuation in drug dose that characterizes injection delivery of drugs; and the devices and methods of this invention are less invasive than many of the prior art devices and surgical techniques, which result in a large number of retinal detachments.

Most, if not all, ophthalmic diseases and disorders are associated with one or more of three types of indications: (1) angiogenesis, (2) inflammation, and (3) degeneration. To treat these disorders, the devices of the present invention permit delivery of anti-angiogenic factors; anti-inflammatory factors; factors that retard cell degeneration, promote cell sparing, or promote cell growth; and combinations of the foregoing. Based on the indications of a particular disorder, one of ordinary skill in the art can administer any suitable molecule or combination of molecules from the three groups at the dosages specified below.

Diabetic retinopathy, for example, is characterized by angiogenesis. This invention contemplates treating diabetic retinopathy by implanting devices delivering one or more anti-angiogenic factors either intraocularly, preferably in the vitreous, or periocularly, preferably in the subTenon's region. We most prefer delivery into the vitreous for this indication. It is also desirable to co-deliver one or more neurotrophic factors, either intraocularly or periocularly, preferably intraocularly, and most preferably intravitreally.

Uveitis involves inflammation. This invention contemplates treating uveitis by intraocular, preferably vitreal or anterior chamber, implantation of devices secreting one or more anti-inflammatory factors.

Retinitis pigmentosa, by comparison, is characterized by retinal degeneration. This invention contemplates treating retinitis pigmentosa by intraocular, preferably vitreal, placement of devices secreting one or more neurotrophic factors.

Age-related macular degeneration involves both angiogenesis and retinal degeneration. This invention contemplates treating this disorder by using the inventive devices to deliver one or more neurotrophic factors intraocularly, preferably to the vitreous, and/or one or more anti-angiogenic factors intraocularly or periocularly, preferably periocularly, most preferably to the sub-Tenon's region.

Glaucoma is characterized by increased ocular pressure and loss of retinal ganglion cells. Treatments for glaucoma contemplated in this invention include delivery of one or more neuroprotective agents that protect cells from excitotoxic damage. Such agents include N-methyl-D-aspartate (NMDA) antagonists, cytokines, and neurotrophic factors, delivered intraocularly, preferably intravitreally.

Any suitable DAM may be delivered according to the devices, systems, and methods of this invention. Such molecules include neurotransmitters, cytokines, lymphokines, neuroprotective agents, neurotrophic factors, hormones, enzymnes, antibodies, and active fragments thereof Three preferred types of BAMs are contemplated for delivery using the devices of the present invention: (1) anti-angiogenic factors, (2) anti-inflammatory factors, and (3) factors that retard cell degeneration, promote cell sparing, or promote cell growth.

The anti-angiogenic factors contemplated for use include vasculostatin, angiostatin, endostatin, anti-integrins, vascular endothelial growth factor inhibitors (VEGF-inhibitors), platelet factor 4, heparinase, and bFGF-binding molecules. The VEGF receptors Flt and Flk are also contemplated. When delivered in the soluble form these molecules compete with the VEGF receptors on vascular endothelial cells to inhibit endothelial cell growth.

VEGF inhibitors may include VEGF-neutralizing chimeric proteins such as soluble VEGF receptors. See Aiello, *PNAS*, 92, 10457 (1995). In particular, they may be VEGF-receptor-IgG chimeric proteins. Another VEGF inhibitor contemplated for use in the present invention is antisense phosphorothiotac oligodeoxynucleotides (PS-ODNs).

Intraocularly, preferably in the vitreous, we contemplate delivery of an anti-angiogenic factor in a dosage range of 50 pg to 500 ng, preferably 100 pg to 100 ng, and most preferably 1 ng to 50 ng per eye per patient per day. For periocular delivery, preferably in the sub-Tenon's space or region, slightly higher dosage ranges are contemplated of up to 1 μg per patient per day.

The anti-inflammatory factors contemplated for use in the present invention include antiflammins (see, e.g., U.S. Pat. No. 5,266,562, incorporated herein by reference), beta-interferon (IFN-β), alpha-interferon (IFN-α), TGF-beta, interleukin-10 (IL-10), and glucocorticoids and mineralocorticoids from adrenal cortical cells. It should be noted that certain BAMs may have more than one activity. For example, it is believed that IFN-α and IFN-β may have activities as both anti-inflammatory molecules and as anti-angiogenic molecules.

Intraocularly, preferably in the vitreous, we contemplate delivery of an anti-inflammatory factor in a dosage range of 50 pg to 500 ng, preferably 100 pg to 100 ng, and most preferably 1 ng to 50 ng per eye per patient per day. For periocular delivery, preferably in the sub-Tenon's space or region, slightly higher dosage ranges are contemplated of up to 1 μg per patient per day.

The factors contemplated for use in retarding cell degeneration, promoting cell sparing, or promoting new cell growth are collectively referred to a herein as "neurotrophic factors". The neurotrophic factors contemplated include neurotrophin 4/5 (NT-4/5), cardiotrophin-1 (CT-1), ciliary neurotrophic factor (CNTF), glial cell line derived neurotrophic factor (GDNF), nerve growth factor (NGF), insulin-like growth factor-1 (IGF-1), neurotrophin 3 (NT-3), brain-derived neurotrophic factor (BDNF), PDGF, neurturin, acidic fibroblast growth factor (aFGF), basic fibroblast growth factor (bFGF), EGF, neuregulins, heregulins, TGF-alpha, bone morphogenic proteins (BMP-1, BMP-2, BMP-7, etc.), the hedgehog family (sonic hedgehog, indian hedgehog, and desert hedgehog, etc.), the family of transforming growth factors (including, e.g., TGFβ-1, TGFβ-2, and TGFβ-3), interleukin 1-B (IL1-β), and such cytokines as interleukin-6 (IL-6), IL-10, CDF/LIF, and beta-interferon (IFN-β). The preferred neurotrophic factors are GDNF, BDNF, NT-4/5, neurturin, CNTF, and CT-1.

Intraocularly, preferably in the vitreous, we contemplate delivery of a neurotrophic factor in a dosage range of 50 pg to 500 ng, preferably 100 pg to 100 ng, and most preferably 1 ng to 50 ng per eye per patient per day. For periocular delivery, preferably in the sub-Tenon's space or region, slightly higher dosage ranges are contemplated of up to 1 μg per patient per day.

Modified, truncated, and mutein forms of the above-mentioned molecules are also contemplated. Further, active fragments of these growth factors (i.e., those fragments of growth factors having biological activity sufficient to achieve a therapeutic effect) are also contemplated. Also contemplated are growth factor molecules modified by attachment of one or more polyethylene glycol (PEG) or other repeating polymeric moieties. Combinations of these proteins and polycistronic versions thereof are also contemplated.

A gene of interest (i.e., a gene that encodes a suitable BAM) can be inserted into a cloning site of a suitable expression vector by using standard techniques. The nucleic acid and amino acid sequences of the human (and other mammalian) genes encoding the above identified BAMs are known. See, e.g., U.S. Pat. Nos. 4,997,929; 5,141,856; 5,364,769; 5,453,361; WO 93/06116; WO 95/30686, incorporated herein by reference.

The expression vector containing the gene of interest may then be used to transfect the desired cell line. Standard transfection techniques such as calcium phosphate co-precipitation, DEAE-dextran transfection or electroporation may be utilized. Commercially available mammalian transfection kits may be purchased from e.g., Stratagene. Transgenic-mouse-derived cell lines can also be used. See, e.g., Hammang et al., *Methods in Neurosci.*, 21, p. 281 (1994).

A wide variety of host/expression vector combinations may be used to express the gene encoding the growth factor, or other BAM(s) of interest.

Suitable promoters include, for example. the early and late promoters of SV40 or adenovirus and other known non-retroviral promoters capable of controlling gene expression.

Useful expression vectors, for example, may consist of segments of chromosomal, non-chromosomal, and synthetic DNA sequences, such as various known derivatives of SV40 and known bacterial plasmids, e.g., pUC, pBlueScript™ plasmids from *E. coli* including pBR322, PCR1, pMB9, and their derivatives.

Expression vectors containing the geneticin (G418) or hygromycin drug selection genes (Southern, P. J., *In Vitro*, 18, p. 315 (1981), Southern, P. J. and Berg, P., *J. Mol. Appl. Genet.*, 1, p. 327 (1982)) are also useful. These vectors can employ a variety of different enhancer/promoter regions to drive the expression of both a biologic gene of interest (e.g., NGF) and/or a gene conferring resistance to selection with toxin such as G418 or hygromycin B. A variety of different mammalian promoters can be employed to direct the expression of the genes for G418 and hygromycin B and/or the biologic gene of interest.

Examples of expression vectors that can be employed are the commercially available pRC/CMV, pRC/RSV, and pCDNA1NEO (In Vitrogen).

If cells of a CNS origin are used, preferably the promoter is selected from the following group:

promoters of hDBH (human dopamine beta hydroxylase) (Mercer et al., *Neuron*, 7, pp. 703–716, (1991)), hTH (human tyrosine hydroxylase) (Kaneda, et al., *Neuron*, 6, pp. 583–594 (1991)), hPNMT (human phenylethanolamine N-methyltransferase) (Baetge et al., *PNAS*, 85, pp. 3648–3652 (1988)), mGFAP (mouse glial fibrillary acidic protein) (Besnard et al., *J. Biol. Chem.*, 266, pp. 18877–18883 (1991)), myelin basic protein (MBP), mNF-L (mouse neurofilament-light subunit) (Nakahira et al., *J. Biol. Chem.*, 265, pp. 19786–19791 (1990)), hPo (human $P_0$, the promoter for the gene encoding the major myelin glycoprotein in the peripheral nervous system) (Lemke et al., *Neuron*, 1, pp. 73–83 (1988)), mMt-1 (mouse metallothionein I), rNSE (rat neuron-specific enolase) (Sakimura, et al., *Gene*, 60, pp. 103–113 (1987)), and the like.

In one preferred embodiment, the phosphoglycerate kinase (PGK) promoter is used. See, e.g., Adra et al., *Gene*, 60, pp. 65–74 (1987). The pPI vector is one preferred expression vector using the PGK promoter to drive the expression of the gene of interest (i.e. the gene encoding the BAM). This vector also uses the SV40 early promoter to drive expression of neo phosphotransferase, a selectable marker. One may optimize or enhance expression of a BAM from the pPI vector by inserting the Kozak sequence and/or the Ig signal peptide. The pPI vector also contains a mutant DHFR gene suitable for MTX amplification.

In another embodiment, the pNUT expression vector, which contains the cDNA of the mutant DHFR and the entire pUC18 sequence including the polylinker, can be used. See, e.g., Aebischer, P., et al., *Transplantation*, 58, pp. 1275–1277 (1994); Baetge et al., *PNAS*, 83, pp. 5454–58 (1986). The pNUT expression vector can be modified such that the DHFR coding sequence is replaced by the coding sequence for G418 or hygromycin drug resistance. The SV40 promoter within the pNUT expression vector can also be replaced with any suitable constitutively expressed mammalian promoter, such as those discussed above.

Increased expression can be achieved by increasing or amplifying the copy number of the transgene encoding the desired molecule, using amplification methods well known in the art. Such amplification methods include, e.g., DHFR amplification (see, e.g., Kaufman et al., U.S. Pat. No. 4,470,461) or glutamine synthetase ("GS") amplification (see, e.g., U.S. Pat. No. 5,122,464, and European published application EP 338,841).

A wide variety of cells may be used. These include well known, publicly available immortalized cell lines as well as dividing primary cell cultures. Examples of suitable publicly available cell lines include, Chinese hamster ovary (CHO), mouse fibroblast (L-M), NIH Swiss mouse embryo (NIH/3T3), African green monkey cell lines (including COS-1, COS-7, BSC-1, BSC40, BMT-10, and Vero), rat adrenal pheochromocytoma (PC12 and PC12A), AT3, rat glial tumor (C6), astrocytes, and other fibroblast cell lines. Primary cells that may be used include EGF-responsive neural stem cells and their differentiated progeny (Reynolds and Weiss, *Science*, 255, pp. 1707–1710 (1992)), bFGF-responsive neural progenitor stem cells derived from the CNS of mammals (Richards et al., *PNAS* 89, pp. 8591–8595 (1992), Ray et al., *PNAS* 90, pp. 3602–3606 (1993)), CNS neural stem cells that are both EGF-responsive and bFGF-responsive, primary fibroblasts, Schwann cells, β-TC cells, Hep-G2 cells, oligodendrocytes and their precursors, myoblasts (including L6 and $C_2C_{12}$ cells), chondrocytes or chondroblasts, and the like.

Conditionally-immortalized cells may also be used. Such cells include cells with temperature sensitive oncogenes, or cells engineered with chimeric genes composed of an oncogene under the direction of an inducible promoter element.

One preferred cell type chosen for the gene transfer technique is the baby hamster kidney (BHK) cell. BHK cells are particularly amenable to MTX amplification, most likely because they do not express a highly functional DHFR gene.

The suitable cell types include cells from allogeneic and xenogeneic sources. A particular advantage to using xenogeneic cells is that in the unlikely event of membrane or device failure, such cells are more likely to be targeted for destruction by the immune system.

For delivery in the eye, it may be particularly beneficial to employ primary cells (including primary cells that can be induced to divide using mitogens such as EGF or bFGF or the like) or cell lines, conditionally-immortalized or otherwise, derived from various regions of the eye. Potentially useful cell types include lens epithelial cells, glial and neuronal elements of the neural retina, photoreceptor cells, retinal pigmented epithelial cells, Schwann cells and other ciliary body cells, and the like. Such cells can be allogeneic or xenogeneic.

As used herein "a biocompatible capsule" means that the capsule, upon implantation in a host mammal, does not elicit a detrimental host response sufficient to result in the rejection of the capsule or to render it inoperable, for example through degradation.

As used herein "an immunoisolatory capsule" means that the capsule upon implantation into a mammalian host minimizes the deleterious effects of the host's immune system on the cells within its core. To be immunoisolatory, the capsule should provide a physical barrier sufficient to prevent detrimental immunological contact between the isolated cells and the host's immune system. The thickness of this physical barrier can vary, but it will always be sufficiently thick to prevent direct contact between the cells and/or substances on either side of the barrier. The thickness of this region generally ranges between 5 and 200 microns; thicknesses of 10 to 100 microns are preferred, and thickness of 20 to 75 microns are particularly preferred.

The exclusion of IgG from the core of the vehicle is not the touchstone of immunoisolation, because in most cases IgG alone is insufficient to produce cytolysis of the target cells or tissues. Thus, for immunoisolatory capsules, jacket nominal molecular weight cutoff(MWCO) values between 50–2000 kD are contemplated. Preferably, the MWCO is between 50–700 kD. Most preferably, the MWCO is between 70–300 kD. See, e.g., WO 92/19195. If immunoisolation is not required, the jacket can be microporous. See, e.g., U.S. Pat. Nos. 4,968,733; 4,976,859; and 4,629,563; all incorporated herein by reference.

A variety of biocompatible capsules are suitable for delivery of molecules according to this invention. Useful biocompatible polymer capsules comprise (a) a core which contains a cell or cells, either suspended in a liquid medium or immobilized within a biocompatible matrix, and (b) a surrounding jacket comprising a membrane which does not contain isolated cells, which is biocompatible, and permits diffusion of the cell-produced BAM into the eye.

Many transformed cells or cell lines are advantageously isolated within a capsule having a liquid core, comprising, e.g., a nutrient medium, and optionally containing a source of additional factors to sustain cell viability and function.

Alternatively, the core may comprise a biocompatible matrix of a hydrogel or other biocompatible matrix material which stabilizes the position of the cells. The term "hydrogel" herein refers to a three dimensional network of cross-linked hydrophilic polymers. The network is in the form of a gel, substantially composed of water, preferably gels being greater than 90% water.

Any suitable matrix or spacer may be employed within the core, including precipitated chitosan, synthetic polymers and polymer blends, microcarriers, and the like, depending upon the growth characteristics of the cells to be encapsulated. Aternatively, the capsule may have an internal scaffold. The scaffold may prevent cells from aggregating and improve cellular distribution within the device. See PCT publication no. WO 96/02646.

Preferably, for implant sites that are not immunologically privileged, such as periocular sites, the capsules are immunoisolatory.

The capsule can be any suitable configuration, including cylindrical, rectangular, disk-shaped, patch-shaped, ovoid, stellate, or spherical. Configurations that tend to lead to migration of the capsules from the site of implantation, such as spherical, are not preferred. For implantations in the vitreous, flat sheets may not be preferred because they may block the visual path to the retina.

Preferably the device has a tether that aids in maintaining device placement during implant and aids in retrieval. Such a tether may have any suitable shape that is adapted to secure the capsule in place. In one embodiment, the tether is shaped like an eyelet, so that suture may be used to secure the tether (and thus the capsule) to the sclera, or other suitable ocular structure. In another embodiment, the tether is continuous with the capsule at one end, and forms a pre-threaded suture needle at the other end. The capsules contemplated here have a minimum core volume of about 1 to 20 µl, most preferably about 1 to 10 µl.

In a hollow fiber configuration, the fiber will have an inside diameter of less than 1000 microns, preferably less than 950 microns. In one series of embodiments, the device is configured to have an 870 µm inner diameter and a length of about 8.5 mm. In another series of embodiments, the device is configured to have a 500 µm inner diameter and a length of 10.5 mm. For implantation in the eye, in a hollow fiber configuration the capsule will preferably be between 0.4 cm to 1.5 cm in length, most preferably between 0.5 to 1.0 cm in length. Longer devices may be accommodated in the eye, however, a curved or arcuate shape may be required for secure and appropriate placement. The hollow fiber configuration is preferred for intraocular placement.

For periocular placement, either a hollow fiber configuration (with dimensions substantially as above) or a flat sheet configuration is contemplated. The upper limit contemplated for a flat sheet is approximately 5 mm×5 mm— assuming a square shape. Other shapes with approximately the same surface area are also contemplated.

The hydraulic permeability will typically be in the range of 1–100 mls/min/$M^2$/mmHg, preferably in the range of 25 to 70 mls/min/$M^2$/mmHg. The glucose mass transfer coefficient of the capsule, defined, measured, and calculated as described by Dionne et al., *ASAIO Abstracts*, p. 99 (1993), and Colton et al., *The Kidney*, eds., Brenner BM and Rector FC, pp. 2425–89 (1981) will be greater than $10^{-6}$ cm/sec, preferably greater than $10^{-4}$ cm/sec.

The capsule jacket may be manufactured from various polymers and polymer blends including polyacrylates (including acrylic copolymers), polyvinyildenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrilelcovinyl chloride), as well as derivatives, copolymers, and mixtures thereof. Capsules manufactured from such materials are described, e.g., in U.S. Pat. Nos. 5,284,761 and 5,158,881, incorporated herein by reference. Capsules formed from a polyether sulfone (PES) fiber, such as those described in U.S. Pat. Nos. 4,976,859 and 4,968,733, incorporated herein by reference, may also be used.

Depending on the outer surface morphology, capsules have been categorized as Type 1 (T1), Type 2 (T2), Type 1/2 (T1/2), or Type 4 (T4). Such membranes are described, e.g., in Lacy et al., "Maintenance Of Normoglycemia In Diabetic Mice By Subcutaneous Xenografts Of Encapsulated Islets." *Science*, 254, pp. 1782–84 (1991), Dionne et al., WO 92/19195 and Baetge, WO 95/05452. We prefer a smooth outer surface morphology.

Capsule jackets with permselective immunoisolatory membranes are preferable for sites that are not immunologically privileged. In contrast, microporous membranes or permselective membranes may be suitable for immunologically privileged sites. For implantation into immunologically privileged sites, we prefer capsules made from the PES membranes.

Figure 3A:
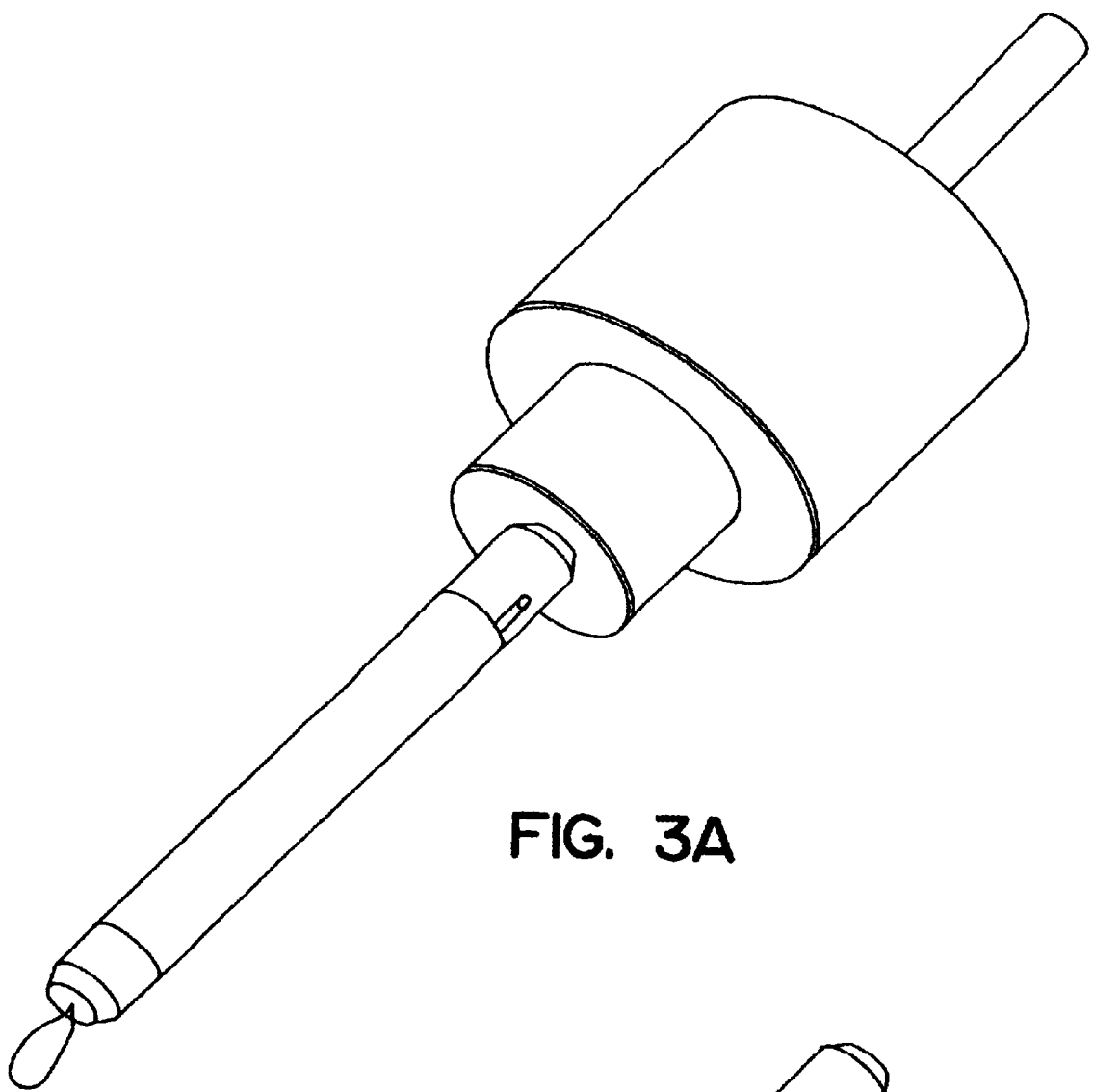
FIG. 3A shows a device with frangible hub assembly for loading.
Figure 3B:
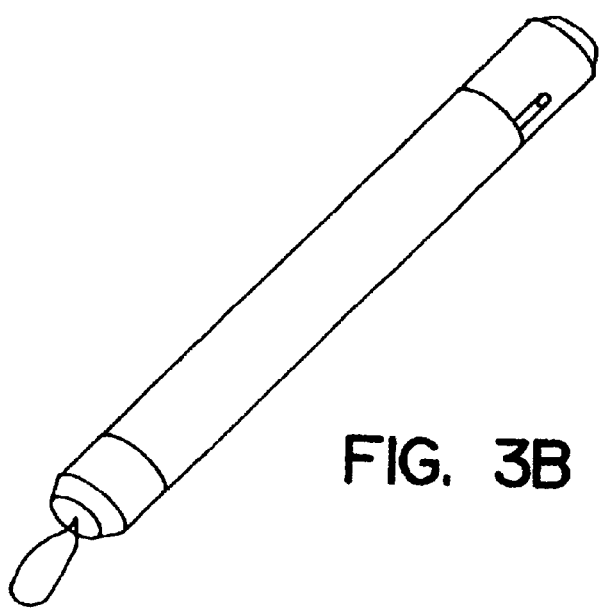
FIG. 3B depicts the device after detachment of the frangible hub. The device has an eyelet for tethering the device in the eye.
Figure 4A:
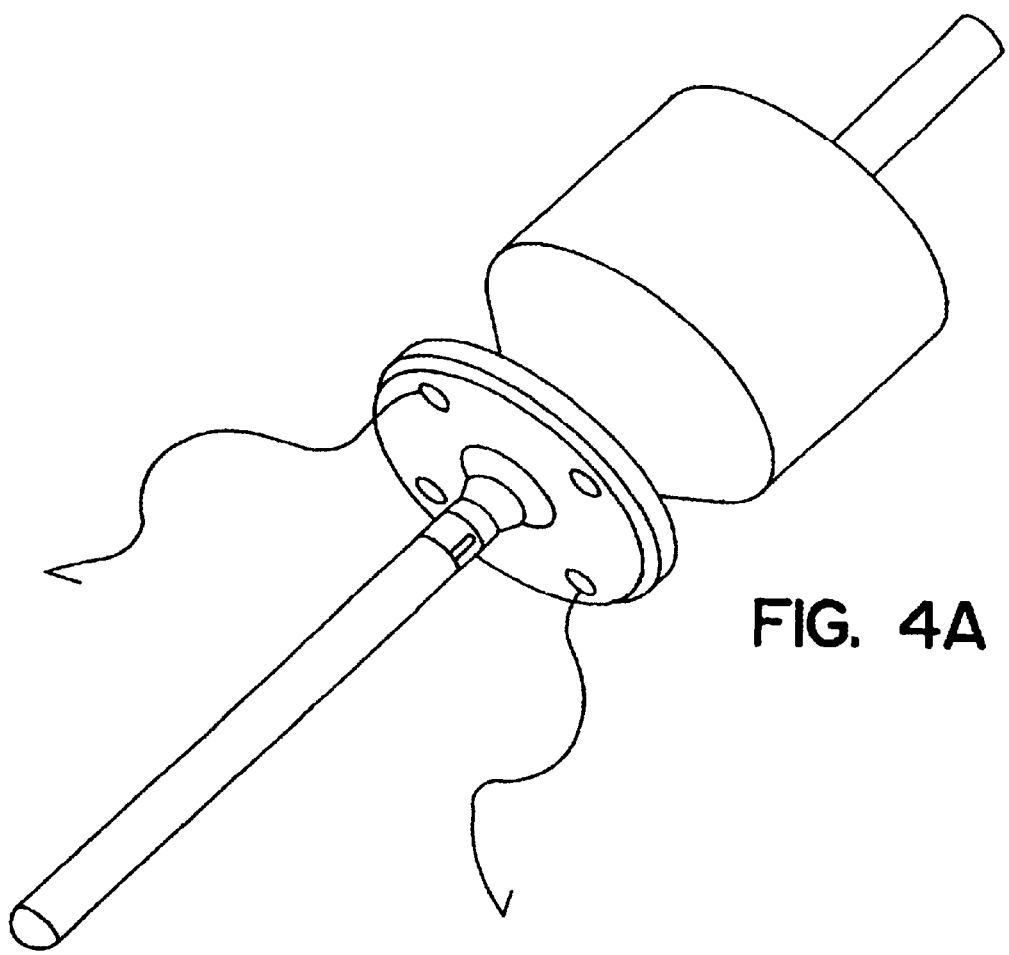
FIG. 4A shows a device with frangible hub assembly for loading.
Figure 4B:
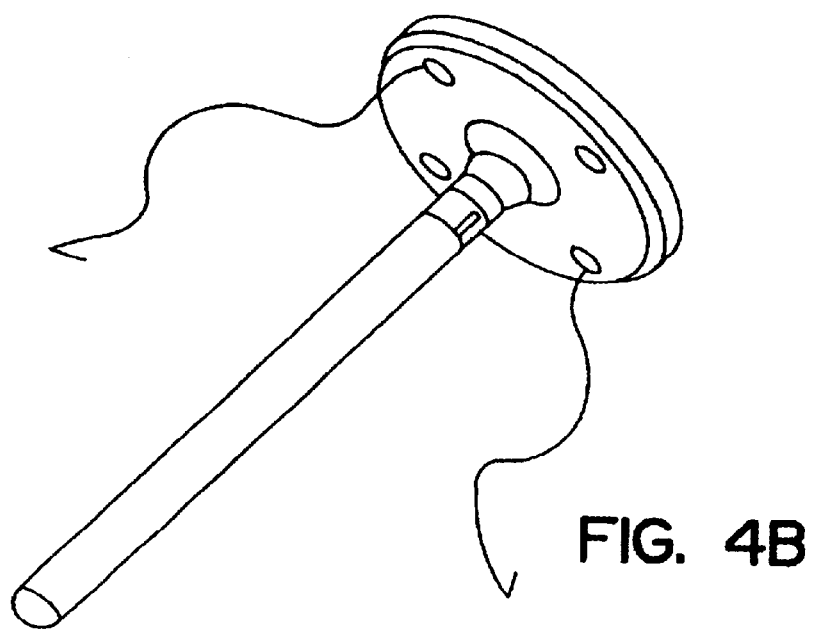
FIG. 4B depicts the device after detachment of the frangible hub. The device has a disk for tethering the device.

Any suitable method of sealing the capsules may be used, including the employment of polymer adhesives and/or crimping, knotting, and heat sealing. These sealing techniques are known in the art. In addition, any suitable "dry" sealing method can also be used. In such methods, a substantially non-porous fitting is provided through which the cell-containing solution is introduced. Subsequent to filling, the capsule is sealed. Such a method is described in copending U.S. application Ser. No. 08/082,407, herein incorporated by reference (see also PCT/US94/07015). That application describes the frangible hub assembly shown diagrammatically in FIGS. 3 and 4 that can be used to conveniently load and seal the devices of this invention.

We contemplate use of the present invention to treat a wide variety of ophthalmic diseases and disorders characterized by but not limited to angiogenesis, inflammation, degeneration, or some combination thereof Some examples of ophthalmic disorders that may be treated by various embodiments of the present invention include uveitis, retinitis pigmentosa, age-related macular degeneration and other acquired disorders, retinopathy, retinal vascular diseases and other vascular anomalies, endophthalmitis, infectious diseases, inflammatory but non-infectious diseases, ocular ischemia syndrome, peripheral retinal degenerations, retinal degenerations and tumors. choroidal disorders and tumors, vitreous disorders, retinal detachment, non-penetrating and penetrating trauma, post-cataract complications, and inflammatory optic neuropathies.

Age-related macular degeneration includes but is not limited to dry age-related macular degeneration, exudative age-related macular degeneration, and myopic degeneration.

Retinopathy includes but is not limited to diabetic retinopathy, proliferative vitreoretinopathy, and toxic retinopathy.

The present invention may be useful for the treatment of ocular neovascularization, a condition associated with many ocular diseases and disorders and accounting for a majority of severe visual loss. For example, we contemplate treatment of retinal ischemia-associated ocular neovascularization, a major cause of blindness in diabetes and many other diseases; corneal neovascularization, which predisposes patients to corneal graft failure; and neovascularization associated with diabetic retinopathy, central retinal vein occlusion, and possibly age-related macular degeneration.

The present invention may also be used to treat ocular symptoms resulting from diseases or conditions that have both ocular and non-ocular symptoms. Some examples include AIDS-related disorders such as cytomegalovirus retinitis and disorders of the vitreous; pregnancy-related disorders such as hypertensive changes in the retina; and ocular effects of various infectious diseases such as tuberculosis, syphilis, lyme disease, parasitic disease, toxocara canis, ophthalmonyiasis, cyst cercosis, and fungal infections.

In one embodiment of the present invention, living cells are encapsulated and surgically inserted (under retrobulbar anesthesia) into the vitreous of the eye. For vitreal placement, the device may be implanted through the sclera, with a portion of the device protruding through the sciera. Most preferably, the entire body of the device is implanted in the vitreous, with no portion of the device protruding into or through the sciera. Preferably the device is tethered to the sclera (or other suitable ocular structure). The tether may comprise a suture eyelet (FIG. 3), or disk FIG. 4), or any other suitable anchoring means. The device can remain in the vitreous as long as necessary to achieve the desired prophylaxis or therapy. Such therapies for example include promotion of neuron or photoreceptor survival or repair, or inhibition and/or reversal of retinal or choroidal neovascularization, as well as inhibition of uveal, retinal, and optic nerve inflammation. This embodiment is preferable for delivering the BAM to the retina.

With vitreal placement, the BAM, preferably a trophic factor, may be delivered to the retina or the RPE. In addition, retinal neovascularization may be best treated by delivering an anti-angiogenic factor to the vitreous.

In another embodiment, cell-loaded devices are implanted periocularly, within or beneath the space known as Tenon's capsule. This embodiment is less invasive than implantation into the vitreous and thus is generally preferred. This route of administration also permits delivery of BAMs (e.g., trophic factors and the like) to the RPE or the retina. This embodiment is especially preferred for treating choroidal neovascularization and inflammation of the optic nerve and uveal tract. In general, delivery from this implantation site will permit circulation of the desired BAM to the choroidal vasculature, the retinal vasculature, and the optic nerve.

According to this embodiment we prefer periocular delivery (implanting beneath Tenon's capsule) of anti-angiogenic molecules, anti-inflammatory molecules (such as cytokines and hormones), and neurotrophic factors to the choroidal vasculature to treat macular degeneration (choroidal neovascularization).

Delivery of anti-angiogenic factors directly to the choroidal vasculature (periocularly) or to the vitreous (intraocularly) using the devices and methods of this invention may reduce the above-mentioned problems and may permit the treatment of poorly defined or occult choroidal neovascularization. It may also provide a way of reducing or preventing recurrent choroidal neovascularization via adjunctive or maintenance therapy.

In a preferred embodiment, the pNUT vector carrying the desired gene or genes is transfected into baby hamster kidney (BHK) cells or $C_2C_{12}$ myoblast cells using a standard calcium phosphate transfection procedure and selected with increasing concentrations of methotrexate (1 $\mu$M to a maximum of 200 $\mu$M) over 8 weeks to produce stable, amplified cell lines. Following this selection, the engineered cells may be maintained in vitro in 50–200 $\mu$M methotrexate, prior to encapsulation.

The present invention contemplates co-delivery of different factors. One of ordinary skill in the art may deliver one or more anti-angiogenic factors, anti-inflammatory factors or factors retarding cell degeneration, promoting cell sparing, or promoting cell growth, depending on the indications of the particular ophthalmic disorder. For example, it may be preferable to deliver one or more neurotrophic factors together with one or more anti-angiogenic factors, or one or more anti-inflammatory molecules.

One example is co-delivery of NT-4/5 with endostatin. In this situation, the neurotrophic factor can promote photoreceptor survival while the heparinase would act as an anti-angiogenic factor.

Co-delivery can be accomplished in a number of ways. First, cells may be transfected with separate constructs containing the genes encoding the described molecules. Second, cells may be transfected with a single construct containing two or more genes and the necessary control elements. We prefer multiple gene expression from a single transcript over expression from multiple transcription units. See, e.g., Macejak, *Nature*, 353, pp. 90–94 (1991); WO 94/24870; Mountford and Smith, *Trends Genet.*, 11, pp. 179–84 (1995); Dirks et al., *Gene*, 128, pp. 247–49 (1993); Martinez-Salas et al., *J. Virology*, 67, pp. 3748–55 (1993) and Mountford et al., *Proc. Natl. Acad. Sci. USA*, 91, pp. 4303–07 (1994).

Third, either two or more separately engineered cell lines can be co-encapsulated, or more than one device can be implanted at the site of interest. And fourth, devices may be implanted in two or more different sites in the eye concurrently, to deliver the same or different BAMs. For example, it may be desirable to deliver a neurotrophic factor to the vitreous to supply the neural retina (ganglion cells to the RPE) and to deliver an anti-angiogenic factor via the sub-Tenon's space to supply the choroidal vasculature. While treatment using more than one device is contemplated and up to five devices per eye, we prefer implantation of three devices or less per eye.

Dosage can be varied by any suitable method known in the art. This includes changing (1) the number of cells per device, (2) the number of devices per eye, or (3) the level of BAM production per cell. Cellular production can be varied by changing, for example, the copy number of the gene for the BAM in the transduced cell, or the efficiency of the promoter driving expression of the BAM. We prefer use of $10^3$ to $10^8$ cells per device, more preferably $5 \times 10^4$ to $5 \times 10^6$ cells per device.

This invention also contemplates use of different cell types during the course of the treatment regime. For example, a patient may be implanted with a capsule device containing a first cell type (e.g., BHK cells). If after time, the patient develops an immune response to that cell type, the capsule can be retrieved, or explanted, and a second capsule can be implanted containing a second cell type (e.g., CHO cells). In this manner, continuous provision of the therapeutic molecule is possible, even if the patient develops an immune response to one of the encapsulated cell types.

Alternatively, capsules with a lower MWCO may be used to further prevent interaction of molecules of the patient's immune system with the encapsulated cells.

The methods and devices of this invention are intended for use in a primate, preferably human host, recipient, patient, subject or individual.

EXAMPLES

Example 1

Preparation and Encapsulation of Cells

BHK-hNGF cells (Winn et al., *PNAS*, 1994) were produced as follows:

The human NGF (hNGF) gene with the rat insulin intron, as described by Hoyle et al., was inserted between the BamHI and SmaI sites of pNUT to be driven by the metallothionein I promoter. The pNLJT-hNGF construct was introduced into BHK cells by using a standard calcium phosphate-mediated transfection method. BHK cells were grown in Dulbecco's modified Eagle's medium/10% fetal bovine serum/antibiotic/antimycotic/L-glutamine (GIBCO) in 5% $CO_2$/95% air and at 37° C. Transfected BHK cells were selected in medium containing 200 μM methotrexate (Sigma) for 3–4 weeks, and resistant cells were maintained as a polyclonal population either with or without 200 μM methotrexate.

The cells were maintained in DMEM with 10% FBS, L-glutamine with 50 μM methotrexate prior to these experiments. The cells were passaged 1 to 2 times per week in the presence of methotrexate. The BHK-hNGF cells and BHK control cells were washed with Hank's buffer, then trypsinized and mixed with Zyderm™ collagen matrix. The cell lines and matrix were loaded into separate Hamilton syringes that were equipped with blunted, 25-gauge needles.

The encapsulation procedure was as follows: The hollow fibers were fabricated from polyether sulfone (PES) with an approximate outside diameter of 720 μm and a wall thickness of approximately 100 μm (AKZO-Nobel Wüppertal, Germany). These fibers are described in U.S. Pat. Nos. 4,976,859 and 4,968,733, herein incorporated by reference.

The devices comprise:
- a semipermeable poly (ether sulfone) hollow fiber membrane fabricated by AKZO Nobel Faser AG;
- a hub membrane segment;
- a light cured methacrylate (LCM) resin leading end; and
- a silicone tether.

The devices had a septal fixture at the proximal end for cellular loading access and were sealed at the distal end. BHK cells were prepared as a single-cell suspension and infused into the septal port at a density of 15K cells per μl after mixing 1:1 with physiologic collagen (Vitrogen: PC-1). After infusing 1.5 μl of the cellular suspension, the septum was removed, and the access port was sealed with LCM 23 resin.

The components of the device are commercially available. The LCM glue is available from Ablestik Laboratories (Newark, Del.); Luxtrak Adhesives LCM23 and LCM24).

Example 2

Implantation of Encapsulated Cells into the Sub-Tenon's Space (under Tenon's Capsule)

The patient is prepared and draped in the usual fashion after a retrobulbar injection of 3 cc 2% xylocaine is given to the eye. A speculum is inserted beneath the upper and lower lids. The operating microscope is brought into position. A perpendicular incision is made through both conjunctiva and Tenon's capsule in the superotemporal quadrant approximately 4 mm back from the limbus. The incision is extended approximately 4–5 mm back from the limbus. At that point, a blunt-tipped scissor is inserted through the incision and is used to bluntly dissect back an additional 5 mm or so on the scleral surface. At that point, a membrane device as described in Example 1 is placed in position through this incision to come to rest on the surface of the sclera. The end of the device that is closest to the limbus has a small loop that is attached to the cell-loaded device. At this point, a #10-0 nylon suture is passed through this loop and sutured into the superficial sclera to anchor the membrane to the sclera. At that point, both Tenon's capsule and the conjunctiva are closed with #6-0 plain gut sutures. The speculum is removed and the procedure is concluded.

Example 3

Implantation of Encapsulated Cells into the Vitreous

The patient is prepared and draped in the usual fashion after a retrobulbar injection of 2% xylocaine is given to the eye. At that point, a speculum is inserted into the upper and lower lids and the microscope is brought into position. A small incision is made through both the conjunctiva and Tenon's capsule parallel to and approximately 4 mm from the limbus in the supranasal quadrant. The area exposed is cauterized with a wet-field cautery apparatus. A 3 mm incision is then made perpendicular to the limbus approximately 4 mm back from the limbus. The incision is made through the sclera and into the vitreous cavity with a #65 blade. Any of the vitreous which presents itself in the incision is cut away and removed. At this point, a membrane device as described in Example 1 is inserted through the incision into the vitreous cavity. At the end of the membrane, there is a small 2 mm loop that is attached to the membrane. The loop remains outside the sciera. The sclera is closed with interrupted #9-0 nylon sutures. The #9-0 nylon sutures are also used to anchor this loop of the device to the sclera. The conjunctiva is closed with #60 plain gut sutures.

Example 4

Delivery of Interferon-α (IFN α-2A or IFN α-2B) in the Treatment of Age-Related Macular Degeneration Candidate cell lines are genetically engineered to express the interferon molecules. Various interferons may be used; however, we prefer to use IFN α-2A or α-2B. More than one interferon molecule may be delivered at one time. Various cell lines can also be utilized, we prefer BHK cells.

Cell lines will be encapsulated in preassembled devices substantially according to example 1. Following the device manufacture, a tether is applied. This tether contains an eyelet through which suture material can be passed. The tether is then used to anchor the device in place to avoid device drift or loss. The cell-loaded devices will be held for a standard period to assure device sterility. The capsule is implanted beneath the Tenon's capsule according to example 2.

Patients that have been diagnosed with angiographically proven subfoveal choroidal neovascularization involving any part of the foveal avascular zone are to be selected for this therapy.

The effects of IFN α-2a therapy are assessed by visual acuity, clinical appearance, and fluorescein angiographic appearance. The clinical appearance of the fundus is assessed subjectively with particular reference to macular elevation by subretinal fluid and the presence of intraretinal hemorrhage.

Devices will be removed using the same preparation and surgical procedure as described above. The device will be placed in vitro and assayed for 24 hours for release of IFN-α. After the assay period, the device will be submitted for routine histological analysis to determine the extent of cell survival.

Example 5

Deliver of HNGF to Neonatal Feline Eyes via Encapsulated BHK-hNGF Cell Line

BHK-hNGF clone 36 cells were produced according to example 1.

The cells were then encapsulated into 4 mm LCM 24 light-cured capsules made from AKZO microporous 10/10 membranes according to example 1. The capsules were implanted in neonatal feline eyes substantially according to example 4 for 1 month.

Results

In vitro tests for NGF-induced neurite outgrowth were performed before and after implantation in the feline eyes. Conditioned medium (CM) from unencapsulated BHK-control and BHK-hNGF cells was passed through a 0.2 μm filter and added to cultures of a PC12 cell subclone, PC12A, grown on 6- or 24-well plates at a density of 200,000 cells per ml to test for the presence of hNGF. Encapsulated cells in the polymeric devices were also tested for their ability to release bioactive hNGF by placing the devices in individual wells of a 24-well plate and allowing them to equilibrate for 1–2 days in serum-free defined PC1 medium (Hycor, Portland, Me.); the medium was then removed and replaced with 1 ml of fresh PC1 for an additional 24 hour. This CM was collected, placed on the PC12A cells, and evaluated. Neurite processes that were equal to or greater than three times the length of the cellbody diameter were scored as positive. In addition, the rate of neurite induction and the stability of the neurites was examined.

The level of NGF secretion was also tested by ELISA. Quantitation of hNGF released from both encapsulated and unencapsulated BHK-hNGF cells was performed by a two-site enzyme immunoassay. The protocol was a modification of that described by Boehringer Mannheim using Nunc-Immuno Maxisorp ELISA plates. After color development (30 min.), the samples were analyzed on a plate reader and measured against recombinant mouse NGF protein standards.

The results were as follows:

| Capsule No. | BAM | ELISA Pre-1* pg/24 h. | ELISA Pre-2* pg/24 hr | ELISA Post Explant | Capsule Histology Cell Survival |
|---|---|---|---|---|---|
| 1 | NGF | 152 | 329 | 268 | (+) |
| 2 | NGF | 271 | 162 | 156 | (+) |
| 7 | Control | nd** | nd | 0 | (+) |
| 8 | Control | nd | nd | 0 | (+) |

*Devices were assayed twice prior to implantation, once prior to shipment to the collaborators' laboratory, and a second time immediately prior to implantation, with a 48-hour time interval between the two assays. "Pre-1" refers to the results of the first assay, and "Pre-2" refers to the results of the second assay.
**"nd" is an abbreviation for "not detected."

In a post explant NGF bioactivity assay, robust neurite outgrowth was seen for devices 1 and 2 (NGF), but not for devices 3 and 4 (control).

A second similar experiment was conducted. The results are as follows:

| Capsule No. | BAM | ELISA Pre pg/24 h. | ELISA Post Explant | Capsule Histology Cell Survival |
|---|---|---|---|---|
| 5 | NGF | 1800 | nd* | (−) |
| 6 | NGF | 3900 | 291 | (+) |
| 18 | Control | nd | nd | (−) |
| 19 | Control | nd | nd | (−) |

*"nd" is an abbreviation for "not detected."

In further experiments, BHK cells that secreted hCNTF or NT4/5 were produced and encapsulated substantially according to Example 1. However, we experienced difficulties mainly related to shipping and handling of these devices, leading to poor cell survival in the capsules. Thus no data for these capsules is presented here. The shipping difficulties included desiccation, kinking, breakage, and long exposure to low temperatures.

Continuing experiments are in progress to deliver various BAMs into normal and transgenic pig eyes. Pig models are considered one of the most appropriate animal models for the human eye, based on size and vasculature.

We claim:

1. A method for delivering a biologically active molecule to the eye comprising:

implanting a capsule into the anterior chamber, posterior chamber, or vitreous of the eye, the capsule comprising a core containing living cells providing a cellular source of the biologically active molecule and a surrounding biocompatible jacket, the jacket permitting diffusion of the biologically active molecule into the eye, the capsule configured in a shape adapted to implantation in the anterior chamber, posterior chamber, or vitreous of the eye and optionally having a tether that is adapted to secure the capsule in place wherein the dosage of the biologically active molecule that diffuses into the eye is between 50 pg and 1000 ng per eye per patient per day.

2. The method of claim 1 herein the tether is selected from the group consisting of a loop, a disk, and a suture eyelet.

3. The method of claim 1 wherein the biologically active molecule is an anti-angiogenic factor.

4. The method of claim 3 wherein the anti-angiogenic factor is selected from the group consisting of vasculostatin; angiostatin, endostatin, anti-integrins, vascular endothelial growth factor inhibitors (VEGF-inhibitors), platelet factor 4, heparinase, bFGF-binding molecules, the VEGF receptor Flt, and the VEGF receptor Flk.

5. A method for treating ophthalmic disorders in a patient suffering therefrom, comprising implanting into one or both eyes of the patient, a biocompatible capsule, the capsule comprising:

(a) a core comprising a cellular source of a biologically active molecule, and (b) a jacket surrounding said core, the jacket comprising a biocompatible material that permits diffusion of the biologically active molecule to the eye in a therapeutically effective amount, wherein the dosage of the biologically active molecule that diffuses into the eye is between 50 pg and 1000 ng per eye per patient per day and wherein the ophthalmic disorder is selected from the group consisting of uveitis, retinitis pigmentosa, glaucoma, age-related macular degeneration, and diabetic retinopathy.

6. The method of claim 5 wherein the biologically active molecule is an anti-angiogenic factor.

7. The method of claim 6 wherein the anti-angiogenic factor is selected from the group consisting of vasculostatin; angiostatin, endostatin, anti-integrins, vascular endothelial growth factor inhibitors (VEGF-inhibitors), platelet factor 4, heparinase, bFGF-binding molecules, the VEGF receptor Flt, and the VEGF receptor Flk.

* * * * *

UNITED STATES PATENT AND TRADEMARK OFFICE
CERTIFICATE OF CORRECTION

PATENT NO.       : 6,436,427 B1                                                    Page 1 of 1
APPLICATION NO. : 09/973325
DATED            : August 20, 2002
INVENTOR(S)      : Hammang et al.

It is certified that error appears in the above-identified patent and that said Letters Patent is hereby corrected as shown below:

At Column 1, line 11, before the TECHNICAL FIELD OF THE INVENTION, the following language should be inserted:

--STATEMENT REGARDING FEDERALLY SPONSORED RESEARCH

This invention was made with U.S. government support under United States NIH Grant No. EY001916. The United States Government has certain rights in the invention.--

Signed and Sealed this

Fourteenth Day of August, 2007

JON W. DUDAS
*Director of the United States Patent and Trademark Office*